(12) United States Patent
Kim et al.

(10) Patent No.: US 9,842,975 B2
(45) Date of Patent: Dec. 12, 2017

(54) LIGHT EMITTING DEVICE PACKAGE

(71) Applicant: LG Innotek Co., Ltd., Seoul (KR)

(72) Inventors: Byung Mok Kim, Seoul (KR); Bo Hee Kang, Seoul (KR); Ha Na Kim, Seoul (KR); Hiroshi Kodaira, Seoul (KR); Yuichiro Tanda, Seoul (KR); Satoshi Ozeki, Seoul (KR)

(73) Assignee: LG INNOTEK CO., LTD., Seoul (KR)

( * ) Notice: Subject to any disclaimer, the term of this patent is extended or adjusted under 35 U.S.C. 154(b) by 0 days.

(21) Appl. No.: 15/082,091

(22) Filed: Mar. 28, 2016

(65) Prior Publication Data

US 2016/0211429 A1    Jul. 21, 2016

Related U.S. Application Data

(63) Continuation of application No. 14/729,771, filed on Jun. 3, 2015, which is a continuation of application (Continued)

(30) Foreign Application Priority Data

Sep. 25, 2012 (KR) .................. 10-2012-0106341

(51) Int. Cl.
*H01L 33/02* (2010.01)
*H01L 33/48* (2010.01)
(Continued)

(52) U.S. Cl.
CPC ............ *H01L 33/62* (2013.01); *A61L 2/08* (2013.01); *A61L 2/10* (2013.01); *H01L 33/38* (2013.01);
(Continued)

(58) Field of Classification Search
USPC ........... 250/239, 338.4, 339.06, 361 R, 362, 250/363.01, 370.01, 393, 455.11, 458.1,
(Continued)

(56) References Cited

U.S. PATENT DOCUMENTS 6,330,741 B1    12/2001   Wright et al.
7,288,797 B2    10/2007   Deguchi et al.
(Continued)

FOREIGN PATENT DOCUMENTS

CN    101015071 A    8/2007
CN    101894901 A    11/2010
(Continued)

*Primary Examiner* — Bernard Souw
(74) *Attorney, Agent, or Firm* — Birch, Stewart, Kolasch & Birch, LLP

(57) ABSTRACT

A light emitting device package including a package body including a first cavity and a second cavity, a pad disposed on a bottom surface of the first cavity, a light emitting device disposed on the second cavity electrically connected to the pad, a heat dissipation member inserted into the package body, the heat dissipation member including a body and expanded portions disposed at a partial edge region of the body and electrode patterns disposed at the package body, wherein the package body has an upper portion and a lower portion disposed under the upper portion, wherein the first cavity including side surfaces and a bottom surface, wherein the second cavity provided in the bottom surface of the first cavity.

21 Claims, 6 Drawing Sheets

Related U.S. Application Data

No. 14/496,486, filed on Sep. 25, 2014, now Pat. No. 9,076,949, which is a continuation of application No. 14/275,725, filed on May 12, 2014, now Pat. No. 8,872,195, which is a continuation of application No. 14/035,700, filed on Sep. 24, 2013, now Pat. No. 8,754,423.

(51) Int. Cl.
| | | |
|---|---|---|
| H01L 33/62 | (2010.01) | |
| H01L 33/64 | (2010.01) | |
| A61L 2/08 | (2006.01) | |
| A61L 2/10 | (2006.01) | |
| H01L 33/38 | (2010.01) | |

(52) U.S. Cl.
CPC .......... *H01L 33/483* (2013.01); *H01L 33/486* (2013.01); *H01L 33/641* (2013.01); *H01L 33/642* (2013.01); *H01L 2224/48091* (2013.01); *H01L 2224/48227* (2013.01); *H01L 2924/15174* (2013.01)

(58) Field of Classification Search
USPC ... 250/483.1, 486.1, 488.1, 552; 257/27, 37, 257/79–82, 88, 98–100, 706, 712, 718, 257/E33.001, E33.066, E33.075, E23.001; 438/27, 106, 116, 122, 126, 127; 362/235, 362
See application file for complete search history.

(56) References Cited

U.S. PATENT DOCUMENTS

| | | | |
|---|---|---|---|
| 7,670,872 B2 | 3/2010 | Yan | |
| 7,910,946 B2 | 3/2011 | Kamada | |
| 7,964,883 B2 | 6/2011 | Mazzochette et al. | |
| 8,071,998 B2 | 12/2011 | Chen | |
| 8,124,990 B2 * | 2/2012 | Kim | H01L 33/06 257/13 |
| 8,304,660 B2 | 11/2012 | Tuan et al. | |
| 8,314,346 B2 | 11/2012 | Hasegawa et al. | |
| 8,502,245 B2 * | 8/2013 | Kim | H01L 33/06 257/13 |
| 8,704,208 B2 * | 4/2014 | Kim | H01L 33/04 257/13 |
| 8,754,423 B2 * | 6/2014 | Kim | H01L 33/641 257/79 |
| 8,773,006 B2 * | 7/2014 | Kim | H01L 33/486 313/45 |
| 8,872,158 B2 * | 10/2014 | Shioda | H01L 33/04 257/13 |
| 8,872,195 B2 * | 10/2014 | Kim | H01L 33/641 257/79 |
| 9,076,940 B2 * | 7/2015 | Yuan | H05B 33/0821 |
| 9,076,949 B2 | 7/2015 | Kim et al. | |
| 9,437,791 B2 | 9/2016 | Kim et al. | |
| 2002/0175621 A1 | 11/2002 | Song et al. | |
| 2003/0116769 A1 | 6/2003 | Song et al. | |
| 2008/0179618 A1 | 7/2008 | Cheng | |
| 2009/0289267 A1 | 11/2009 | Burdalski et al. | |
| 2010/0164345 A1 | 7/2010 | Juan et al. | |
| 2010/0181105 A1 | 7/2010 | Hitomi et al. | |
| 2010/0182792 A1 | 7/2010 | Hsiao et al. | |
| 2011/0068358 A1 | 3/2011 | Kuo et al. | |
| 2011/0169037 A1 | 7/2011 | Hasegawa et al. | |
| 2012/0056217 A1 * | 3/2012 | Jung | H01L 25/0753 257/89 |
| 2012/0061695 A1 | 3/2012 | Kim | |
| 2012/0261693 A1 * | 10/2012 | Chen | H01L 33/642 257/98 |
| 2012/0286319 A1 | 11/2012 | Lee et al. | |
| 2012/0314419 A1 | 12/2012 | Sung | |
| 2013/0049563 A1 | 2/2013 | Kim et al. | |
| 2013/0049564 A1 * | 2/2013 | Jung | H01L 33/641 313/45 |
| 2013/0137201 A1 | 5/2013 | Burdalski et al. | |
| 2013/0271983 A1 | 10/2013 | Leshniak et al. | |
| 2014/0084182 A1 | 3/2014 | Kim et al. | |
| 2014/0312380 A1 * | 10/2014 | Jung | H01L 25/0753 257/99 |
| 2015/0014723 A1 * | 1/2015 | Atanackovic | H01L 33/44 257/98 |
| 2015/0214453 A1 | 7/2015 | Jung et al. | |
| 2015/0270463 A1 * | 9/2015 | Kim | A61L 2/08 257/99 |
| 2016/0118563 A1 * | 4/2016 | Jung | H01L 25/0753 257/98 |
| 2016/0126426 A1 * | 5/2016 | Kim | H01L 33/486 257/98 |

FOREIGN PATENT DOCUMENTS

| | | |
|---|---|---|
| EP | 1 760 784 A2 | 3/2007 |
| JP | 2002-353515 A | 12/2002 |
| JP | 2009-94213 A | 12/2002 |
| JP | 2003-197974 A | 7/2003 |
| JP | 2006-93565 A | 4/2006 |
| JP | 2006-303366 A | 11/2006 |
| JP | 2008-288536 A | 11/2008 |
| JP | 2010-87181 A | 4/2010 |
| JP | 2010-171157 A | 8/2010 |
| JP | 5167977 B2 | 11/2010 |
| JP | 2011-205009 A | 10/2011 |
| KR | 10-0678848 B1 | 1/2007 |

* cited by examiner

LIGHT EMITTING DEVICE PACKAGE

CROSS REFERENCE TO RELATED APPLICATION

This application is a Continuation application of U.S. application Ser. No. 14/729,771, filed on Jun. 3, 2015, which is a Continuation application of U.S. application Ser. No. 14/496,486, filed on Sep. 25, 2014, now U.S. Pat. No. 9,076,949, issued Jul. 7, 2015, which is a Continuation application of U.S. application Ser. No. 14/275,725, filed May 12, 2014, now U.S. Pat. No. 8,872,195, issued Oct. 28, 2014, which is a Continuation application of U.S. application Ser. No. 14/035,700, filed Sep. 24, 2013, now U.S. Pat. No. 8,754,423, issued Jun. 17, 2014, which claims priority under 35 U.S.C. §119 to Korean Patent Application No. 10-2012-0106341, filed in Korea on Sep. 25, 2012, which are hereby incorporated in their entirety by reference as if fully set forth herein.

TECHNICAL FIELD

Embodiments relate to light emitting device packages.

BACKGROUND

Light emitting devices, such as Light Emitting Diodes (LEDs) or Laser Diodes (LDs), which use group III-V or group II-VI compound semiconductors, are capable of emitting light of various colors, such as red, green, blue, and ultraviolet light and the like, owing to developments of device materials and thin film growth technologies. Moreover, these light emitting devices are capable of emitting white light with high efficiency through use of a fluorescent substance or color combination, and have advantages of low power consumption, semi-permanent lifespan, fast response time, safety and environmental friendliness as compared to conventional light sources, such as fluorescent lamps, incandescent lamps and the like.

Accordingly, application sectors of light emitting devices are expanded up to transmitting modules of optical communication means, LED backlights to replace Cold Cathode Fluorescence Lamps (CCFLs) which serve as backlights of Liquid Crystal Display (LCD) apparatuses, white LED lighting apparatuses to replace fluorescent lamps or incandescent lamps, head lights of vehicles and traffic lights.

A light emitting device package includes a first electrode and a second electrode arranged over a package body and a light emitting device arranged at a lower surface of the package body and electrically connected to the first electrode and the second electrode.

FIG. 1 is a view illustrating a conventional light emitting device package.

The light emitting device package 100 may include package bodies 110a, 110b, and 110c, which internally define a cavity, and a light emitting device 140 placed on a bottom surface of the cavity. A heat dissipation member 130 may be placed in the package bodies 110a and 110b below the package body 110c. The heat dissipation member 130 and the light emitting device 140 may be fixed via a conductive adhesive layer (not shown).

The cavity is filled with a molding part 150 to surround and protect the light emitting device 140. The molding part 150 may contain a fluorescent substance 160. The fluorescent substance 160 is excited by a first wavelength band of light emitted from the light emitting device 140, thereby emitting a second wavelength band of light.

However, the conventional light emitting device package has the following problems.

In FIG. 1, the heat dissipation member 130 may be formed of a highly thermally conductive material such that heat generated from the light emitting device 140 of the light emitting device package 100 is emitted through the heat dissipation member 130.

In this case, if thermal expansion of the heat dissipation member 130 occurs, this may cause damage to the light emitting device 140. For this reason, a ceramic layer 120, for example, may be placed over the heat dissipation member 130 to prevent damage to the light emitting device 140 due to thermal expansion of the heat dissipation member 130.

However, when the ceramic layer 120 is provided over the heat dissipation member 130, stress may be applied to the ceramic layer 120 above the boundary of the heat dissipation member 130 and the package body 110b due to mismatch between the coefficient of thermal expansion of the heat dissipation member 130 and that of the package body 110b during a co-firing process for fabrication of a ceramic package. This may cause cracking in the ceramic layer 120 within the co-fired package as exemplarily shown in region 'A' of FIG. 1. That is, the ceramic layer 120 may be damaged by coefficient of thermal expansion mismatch between different kinds of materials, and deterioration in the hermetic seal durability of the light emitting device package 100 may cause lifespan reduction after extended operation or upon operation under high humidity environments.

SUMMARY

Embodiments provide a light emitting device package having enhanced hermetic seal durability.

In one embodiment, a light emitting device package includes a package body, at least one electrode pattern placed on the package body, at least one light emitting device electrically connected to the electrode pattern, a heat dissipation member disposed in the package body with thermally contacting to the light emitting device, and an anti-fracture layer, placed on the heat dissipation member, wherein the anti-fracture layer vertically overlaps with at least a partial region of the heat dissipation member.

The anti-fracture layer may have an open region and the light emitting device may be located in the open region.

The heat dissipation member may be formed of at least one of copper (Cu), tungsten (W) or copper tungsten (CuW).

The package body may include a plurality of first ceramic layers.

The anti-fracture layer may be constituted by a second ceramic layer.

The heat dissipation member may have a first horizontal cross sectional area and a second horizontal cross sectional area different from the first horizontal cross sectional area.

A horizontal cross sectional area of the heat dissipation member at a height corresponding to one first ceramic layer may be different from a horizontal cross sectional area of the heat dissipation member at a height corresponding to the other first ceramic layer The heat dissipation member may be provided with an expanded portion at a region corresponding to a boundary of different first ceramic layers.

The anti-fracture layer may be consisted of a second ceramic layer.

A thickness of the second ceramic layer comprising the anti-fracture layer may be 0.5 to 1 times a smallest thickness of one of the first ceramic layers of the package body having different thicknesses.

An area of the open region of the anti-fracture layer may be less than one of a cross sectional area of the heat dissipation member in a direction toward the light emitting device.

The area of the open region of the anti-fracture layer may be less than a minimum cross sectional area of the heat dissipation member.

An area of the open region of the anti-fracture layer may be less than a maximum cross sectional area of the heat dissipation member and greater than a minimum cross sectional area of the heat dissipation member.

The heat dissipation member may have the greatest cross sectional area in a direction toward the light emitting device.

A length of one side of the heat dissipation member in a direction toward the light emitting device may be 1.1 to 1.2 times a length of one side of the heat dissipation member in an opposite direction.

The light emitting device package may further include a third ceramic layer placed between the heat dissipation member and the anti-fracture layer, and the light emitting device may thermally come into contact with the heat dissipation member through the third ceramic layer.

The light emitting device may emit near-ultraviolet or deep-ultraviolet light.

At least one of the package body and the anti-fracture layer may include at least one of $SiO_2$, $Si_xO_y$, $Si_3N_y$, $SiO_xN_y$, $Al_2O_3$, or AlN.

In accordance with another aspect, a light emitting device package includes a package body, at least one electrode pattern placed on the package body, at least one light emitting device electrically connected to the electrode pattern, and a heat dissipation member disposed in the package body with thermally contacting to the light emitting device, the heat dissipation member being provided with an expanded portion at a partial edge region thereof, wherein a region of the heat dissipation member except for the expanded portion has the greatest cross sectional area in a direction toward the light emitting device.

BRIEF DESCRIPTION OF THE DRAWINGS

Arrangements and embodiments may be described in detail with reference to the following drawings in which like reference numerals refer to like elements and wherein.

DESCRIPTION OF SPECIFIC EMBODIMENTS

Hereinafter, embodiments will be described with reference to the annexed drawings.

In the following description of the embodiments, it will be understood that, when each element is referred to as being formed "on" or "under" the other element, one element can be directly "on" or "under" the other element or the two elements can be indirectly formed with intervening one or more other elements therebetween. Also, it will also be understood that "on" or "under" one element may contain the meaning of upward or downward on the basis of the element.

Figure 1:
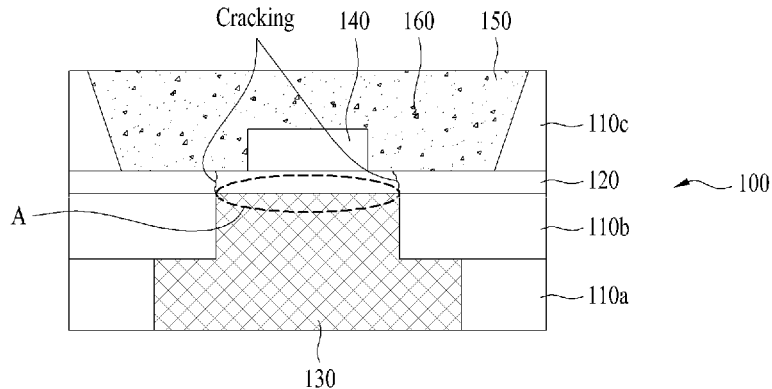
FIG. 1 is a view illustrating a conventional light emitting device package.
Figure 2:
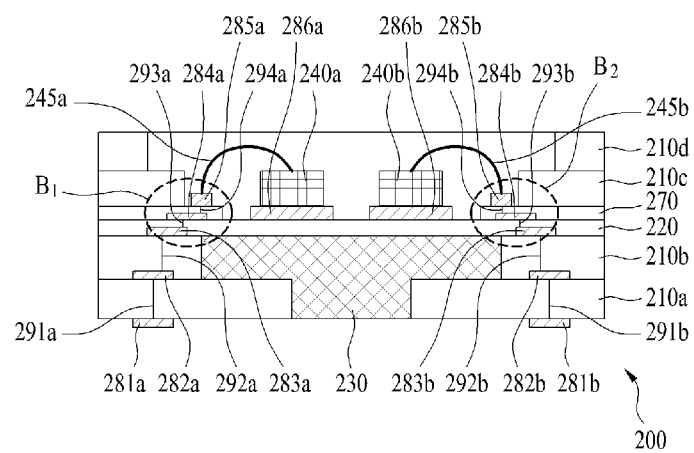
FIG. 2 is a sectional view illustrating an embodiment of a light emitting device package.

FIG. 2 is a sectional view illustrating an embodiment of a light emitting device package.

The light emitting device package, designated by reference numeral 200, according to the embodiment includes a package body consisting of a plurality of first ceramic layers 210a, 210b, 210c and 210d. The package body may be realized using High Temperature Co-fired Ceramics (HTCC) or Low Temperature Co-fired Ceramics (LTCC) technologies.

In the case of the package body taking the form of a multilayered ceramic substrate, respective layers may have the same thickness or different thicknesses. The package body may be formed of an insulating material, such as nitrides or oxides. For example, the package body may be formed of $SiO_2$, $Si_xO_y$, $Si_3N_y$, $SiO_xN_y$, $Al_2O_3$, or AlN.

The plurality of first ceramic layers 210a, 210b, 210c, and 210d may have different widths. Some of the first ceramic layers 210a and 210b may constitute the bottom of the light emitting device package 200 or the bottom of a cavity, and the other first ceramic layers 210c and 210d may constitute a sidewall of the cavity.

At least one of a light emitting device may be arranged on a bottom surface of the cavity constituted of the plurality of ceramic layers as described above. In the present embodiment, two light emitting devices 204a and 240b are arranged. The cavity may be filled with a molding part (not shown) to surround the light emitting devices 240a and 240b and wires 245a and 245b. The molding part may contain a silicon resin or fluorescent substance (not shown), although the disclosure is not limited thereto. The fluorescent substance may convert a first wavelength band of light emitted from the light emitting devices 240a and 240b into a second longer-wavelength band of light. For example, if a first wavelength band is an ultraviolet band, a second wavelength band may be a visible light band. If the light emitting devices 240a and 240b emit ultraviolet light, more specifically, near-ultraviolet light or deep-ultraviolet light, the molding part may contain no fluorescent substance. Ultraviolet light may be electromagnetic radiation with a wavelength of 10 nm to 397 nm. More particularly, ultraviolet light with a wavelength of 290 nm to 397 nm may be referred to as near-ultraviolet light, and ultraviolet light with a wavelength of 190 nm to 290 nm may be referred to as deep-ultraviolet light.

Metal may be deposited or plated on the molding part such that the molding part 250 is coupled to a glass cap or lid using Eutectic bonding, welding, or the like to achieve a hermetic seal. Alternatively, the molding part 250 may be stepped similar to the plurality of first ceramic layers 210c and 210d such that an anti-reflective coated glass plate may be bonded to a stepped recess using an adhesive (e.g., UV setting adhesive bonding, or thermosetting adhesive bonding) to achieve a hermetic seal.

In a case of UV light emitting device, deterioration and discoloration may be caused to the molding part. So, phosphor film or phosphor plate having a resistance to UV may be formed instead of the molding part.

Light emitting devices may include Light Emitting Diodes (LEDs) using multiple compound semiconductor layers, for example, group III-V semiconductor layers. These light emitting devices may be colored light emitting devices to emit blue, green, or red light, or may be UV light emitting devices to emit ultraviolet (UV) light.

The above-described light emitting devices 240a and 240b may be vertical light emitting devices or horizontal light emitting devices. Each light emitting device 240a or 240b may include a light emitting structure that consists of a first conductive type semiconductor layer, an active layer, and a second conductive type semiconductor layer.

The first conductive type semiconductor layer may be formed of a semiconductor compound, for example, group III-V or group II-VI compound semiconductors. Additionally, a first conductive dopant may be doped. If The first conductive type semiconductor layer is an n-type semiconductor layer, the first conductive dopant is an n-type dopant including Si, Ge, Sn, Se and Te, although the disclosure is not limited thereto.

The first conductive type semiconductor layer may be provided alone or along with an undoped semiconductor layer therebelow, although the disclosure is not limited thereto.

The undoped semiconductor layer serves to improve crystallization of The first conductive type semiconductor layer. The undoped semiconductor layer may be equal to The first conductive type semiconductor layer, except for the fact that the undoped semiconductor layer is not doped with the n-type dopant, and thus has lower electric conductivity than The first conductive type semiconductor layer.

The active layer may be formed on The first conductive type semiconductor layer. The active layer serves to emit light having energy determined by an intrinsic energy-band of a constituent material thereof (i.e. a light emitting material) via combination of electrons introduced through The first conductive type semiconductor layer and holes introduced through The second conductive type semiconductor layer that will be formed later.

The active layer may have at least any one of a double hetero junction structure, a single well structure, a multiple well structure, a quantum-wire structure, or a quantum-dot structure. For example, the active layer may have a multiple quantum well structure via injection of trimethylgallium gas (TMGa), ammonia gas ($NH_3$), nitrogen gas ($N_2$), and trimethylindium gas (TMIn), although the disclosure is not limited thereto.

The active layer may include a well layer and a barrier layer, which have at least one pair configuration of InGaN/GaN, InGaN/InGaN, GaN/AlGaN, InAlGaN/GaN, GaAs (InGaAs)/AlGaAs, and GaP(InGaP)/AlGaP, for example, although the disclosure is not limited thereto. The well layer may be formed of a material having a smaller band gap than that of the barrier layer.

A conductive clad layer (not shown) may be disposed on the active layer. The conductive clad layer may be formed of a semiconductor having a greater band gap than that of the barrier layer of the active layer. For example, the conductive clad layer may include GaN, AlGaN, InAlGaN, or superlattice structure. In addition, the conductive clad layer may be an n-type or p-type doped layer.

The second conductive type semiconductor layer may be disposed on the active layer. The second conductive type semiconductor layer may be formed of a semiconductor compound, for example, group III-V compound semiconductors doped with a second conductive dopant. The second conductive type semiconductor layer may include, for example, a semiconductor material having a composition equation of $In_xAl_yGa_{1-x-y}N$ ($0 \le x \le 1$, $0 \le y \le 1$, $0 \le x+y \le 1$). If The second conductive type semiconductor layer is a p-type semiconductor layer, the second conductive dopant is a p-type dopant including Mg, Zn, Ca, Sr, Ba, etc., although the disclosure is not limited thereto.

Alternatively, differently from the above description, The first conductive type semiconductor layer may include a p-type semiconductor layer, and The second conductive type semiconductor layer may include an n-type semiconductor layer. In addition, a third conductive semiconductor layer including an n-type or p-type semiconductor layer may be formed on the first conductive type semiconductor layer. As such, the above-described light emitting devices 240a and 240b may include at least any one of n-p, p-n, n-p-n, p-n-p junction structures.

In the present embodiment, the package body consists of the first ceramic layers 210a, 210b, 210c and 210d formed of inorganic materials. Even if the light emitting devices include deep-UV LEDs to emit UV light having a wavelength of about 280 nm, or near-UV LEDs to emit UV light having a wavelength of about 365~405 nm, the package body is free from discoloration or decomposition due to UV light emitted from the light emitting devices, which enables maintenance of reliability of a light emitting module.

The present embodiment describes the package body as consisting of the four first ceramic layers 210a, 210b, 210c and 210d having the same thickness, the package body may consist of a greater number of first ceramic layers, and the respective first ceramic layers may have different thicknesses.

In FIG. 2, the light emitting devices 240a and 240b are placed on a surface of the package body, and thermally contact to a heat dissipation member 230 through conductive adhesive layers 286a and 286b and a third ceramic layer 220. The heat dissipation member 230 may be formed of a highly thermally conductive material, and more particularly formed of at least one of copper (Cu), tungsten (W) or copper tungsten (CuW). Although FIG. 2 illustrates only one heat dissipation member 230, two or more discrete heat dissipation members may be arranged.

The heat dissipation member 230 may be placed within the first ceramic layers 210a and 210b. The third ceramic layer 220 and a anti-fracture layer 270 may be sequentially placed above the heat dissipation member 230 and the first ceramic layers 210a and 210b. The anti-fracture layer 270 may be formed as a second ceramic layer.

The anti-fracture layer 270 may have a partial open region or a center open region. The aforementioned third ceramic layer 220 may be exposed through the open region, and the light emitting devices 240a and 240b may be arranged on a partial exposed region of the third ceramic layer 220. In this way, the light emitting devices 240a and 240b may thermally come into contact with the heat dissipation member 230 through the third ceramic layer 220. In addition, the anti-fracture layer 270 may overlap with at least a partial peripheral region of the heat dissipation member 230.

The first ceramic layers 210c and 210d comprise the sidewall of the cavity. Electric connection of the light emitting devices 240a and 240b within the light emitting device package 200 will be described below.

A plurality of first electrode patterns 281a to 284a and a plurality of second electrode patterns 281b to 284b are arranged on the plurality of first ceramic layers 210a and 210b, the third ceramic layer 220, and the anti-fracture layer 270. Connection electrodes 291a to 293a and 291b to 293b are respectively arranged between the first electrode patterns 281a to 284a and between the second electrode patterns 281b to 284b.

Arrangement of electrodes and electrode patterns will now be described in detail.

The heat dissipation member 230 may be located within the first ceramic layers 210a and 210b, the anti-fracture layer 270 may be provided with a first bonding pad 285 and a second bonding pad 285b, and the light emitting devices 240a and 240b may be bonded respectively to the first bonding pad 285a and the second bonding pad 285 via the wires 245a and 245b. In addition, the first bonding pad 285a and the second bonding pad 285b may be electrically connected to the first electrode pattern 284a and the second electrode pattern 284b via the connection electrodes 294a and 294b, respectively.

The aforementioned connection electrodes 291a to 294a and 291b to 294b may be formed by perforating holes in the first ceramic layers 210a and 210b, the third ceramic layer 220, and the anti-fracture layer 270, and then filling the perforated holes with a conductive material.

In FIG. 2, the heat dissipation member 230 and the first and second electrode patterns 281a and 281b are exposed under the first ceramic layer 210a to thereby come into electrical contact with a circuit board. The heat dissipation member 230 may act as an electrode pattern.

Figure 3A:
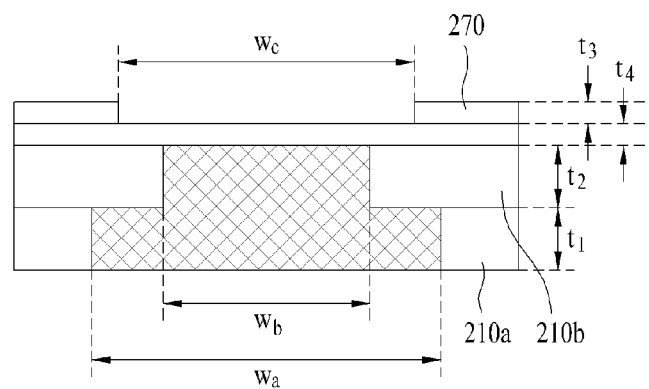
FIGS. 3A to 3C are views schematically illustrating embodiments of a positional relationship between a heat dissipation member and a anti-fracture layer of FIG. 2.
Figure 3:
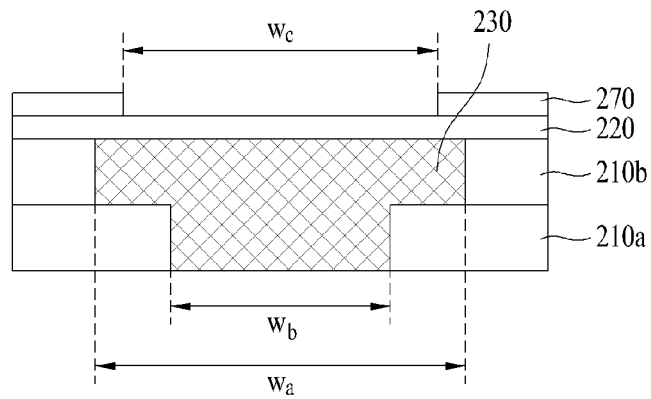
Figure 3:
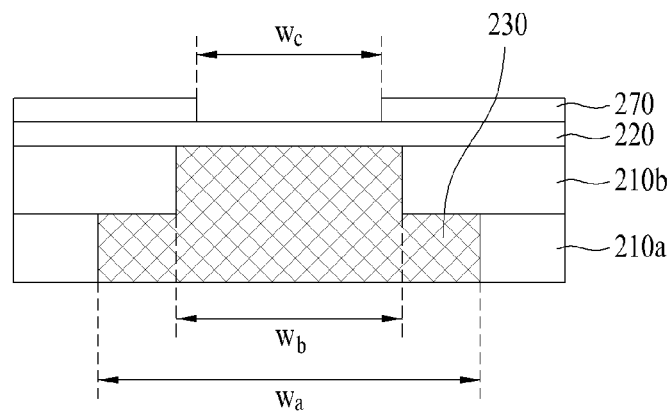

FIGS. 3A to 3C are views schematically illustrating embodiments of a positional relationship between the heat dissipation member and the anti-fracture layer of FIG. 2.

In FIG. 3A, the heat dissipation member 230 has a width $W_a$ at a height corresponding to the first ceramic layer 210a and a width $W_b$ at a height corresponding to the first ceramic layer 210b, the width $W_a$ being greater than the width $W_b$. The open region of the anti-fracture layer 270 has a width $W_c$, which may be less than the width $W_a$ at the height corresponding to the first ceramic layer 210a and greater than the width $W_b$ at the height corresponding to the first ceramic layer 210b. The width Wa may be 1.1~1.2 times the width Wb. The width $W_a$ may be in a range of 3.0 mm to 3.4 mm, and the width $W_b$ may be in a range of 2.5 mm to 3.0 mm.

That is, a portion of the heat dissipation member 230 coming into contact with the light emitting devices 240a and 240b has a smaller width or area than that of an opposite radiation portion, which may cause radiation enhancement.

In addition, since the width $W_c$ of the open region of the anti-fracture layer 270 is less than the width $W_a$ of the heat dissipation member 230 at the height corresponding to the first ceramic layer 210a, the anti-fracture layer 270 may resist stress caused by thermal expansion of the heat dissipation member 230, thereby preventing cracking at the third ceramic layer 220. In addition, in consideration of the fact that the light emitting devices 240a and 240b may be arranged at the exposed region of the third ceramic layer 220, the width $W_c$ of the open region of the anti-fracture layer 270 may be greater than the width Wb of the heat dissipation member 230 at the height corresponding to the first ceramic layer 210b.

In FIG. 3A, a thickness $t_1$ of one first ceramic layer 210a may be equal to a thickness $t_2$ of the other first ceramic layer 210b. In addition, a thickness $t_3$ of the anti-fracture layer 270, which may serve as the second ceramic layer, may be equal to a thickness $t_4$ of the third ceramic layer 220 and may be 0.5~1 times the thickness $t_1$ of the first ceramic layer 210a. In the present embodiment, the thicknesses $t_1$ and $t_2$ of the first ceramic layers 210a and 210b may be 0.6 mm, the thickness $t_3$ of the anti-fracture layer 270 may be 0.4 mm, and the thickness $t_4$ of the third ceramic layer 220 may be 0.2 mm. The thickness $t_1$ of the first ceramic layer 210a is given according to one embodiment of the light emitting device package 200. In another embodiment, for example, the thickness $t_3$ of the anti-fracture layer 270 may be equal to the thickness $t_1$ of the first ceramic layer 210a.

In the embodiment exemplarily shown in FIG. 3B, the top width of the heat dissipation member 230 is equal to the bottom width of the embodiment exemplarily shown in FIG. 3A. More specifically, the width $W_a$ of the heat dissipation member 230 at the height corresponding to the first ceramic layer 210b is greater than the width $W_b$ of the heat dissipation member 230 at the height corresponding to the first ceramic layer 210a. In this case, stress caused by thermal expansion of the heat dissipation member 230, in particular, may be concentrated on an edge of the heat dissipation member 230. Since the width $W_c$ of the open region of the anti-fracture layer 270 is less than the width $W_a$ of the heat dissipation member 230 at the height corresponding to the first ceramic layer 210b, the anti-fracture layer 270 may act to alleviate stress to be concentrated on a region of the third ceramic layer 220 corresponding to the edge of the heat dissipation member 230.

In addition, a region of the heat dissipation member 230 proximate to the light emitting device has a greater width, which may ensure easy heat transfer from the light emitting device to the heat dissipation member 230. However, it is noted that a region of the heat dissipation member 230 provided with an expanded portion 235 has a greater width than the region of the heat dissipation member 230 proximate to the light emitting device.

The embodiment exemplarily shown in FIG. 3C is similar to the embodiment of FIG. 3A, but the width $W_c$ of the open region of the anti-fracture layer 270 is less than the width $W_b$ of the heat dissipation member 230 at the height corresponding to the first ceramic layer 210b. With this configuration, the anti-fracture layer 270 may act to alleviate stress to be concentrated on a region of the third ceramic layer 220 corresponding to the edge of the heat dissipation member 230.

Figure 4:
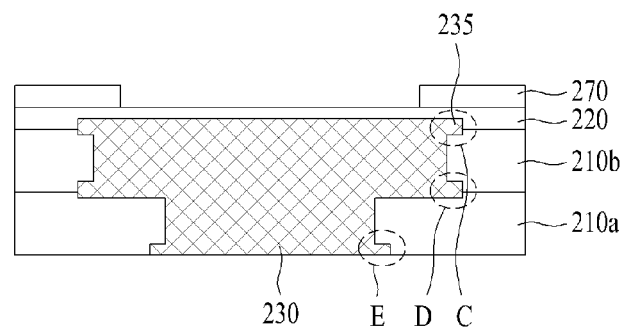
FIGS. 4A to 4C are views illustrating different embodiments of the anti-fracture layer of FIG. 2.
Figure 4:
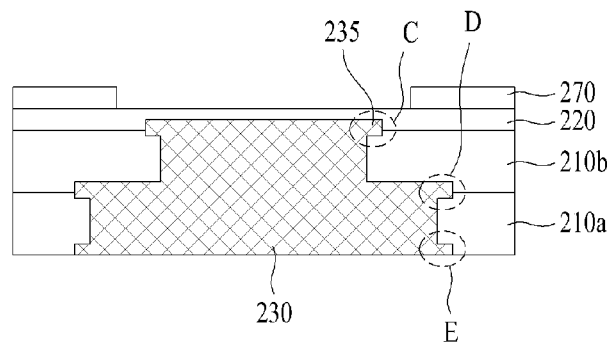
Figure 4:
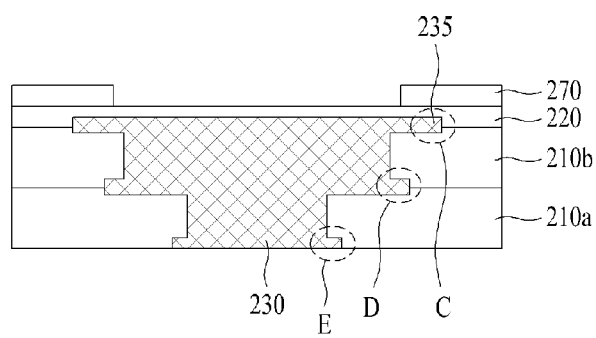

FIGS. 4A to 4C are views illustrating different embodiments of the anti-fracture layer of FIG. 2.

In the case in which the heat dissipation member 230 has a configuration as exemplarily shown in FIG. 3A or FIG. 3C, in particular, the heat dissipation member 230 may be separated downward of the drawing due to coefficient of thermal expansion mismatch when heat is applied to different kinds of materials constituting the first ceramic layers 210a and 210b.

Accordingly, the heat dissipation member 230 may have different horizontal cross sectional areas or horizontal side lengths at different heights corresponding respectively to the first ceramic layers 210a and 210b. Accordingly, the heat dissipation member 230 may have a first horizontal cross sectional area and a second horizontal cross sectional area different from the first horizontal cross sectional area. In addition, the heat dissipation member 230 may have an expanded portion corresponding to a boundary of the first ceramic layers 210a and 210b.

Accordingly, as exemplarily shown in FIGS. 4A and 4B, an expanded portion 235 may be formed at a partial region of the heat dissipation member 230 to secure the heat dissipation member 230. The expanded portion 235 may protrude from an uppermost edge of the heat dissipation member 230, and may be supported by the first ceramic layer 210b at regions C and D.

In FIG. 4C, the expanded portions 235 are respectively formed at the regions C and D to firmly secure the heat dissipation member 230 to the first ceramic layers 210a and 210b. Although FIGS. 4A to 4C illustrate an additional expanded portion formed at a region E, the level of contribution to securing of the heat dissipation member 230 may be less than that of the expanded portions formed at the region C and the region D.

In the above-described embodiments, the expanded portion 235 may be circularly formed at the edge of the heat dissipation member 230, although it is illustrated as being present at either side in the cross sectional view. One expanded portion 235 may be located between two neighboring layers, for example, between the first ceramic layers 210a and 210b or between the first ceramic layer 210b and the third ceramic layer 220.

In the above-described embodiments of the light emitting device package 200, the third ceramic layer 220 and the anti-fracture layer 270 may endure stress caused by thermal expansion of the heat dissipation member 230 even if the heat dissipation member 230 thermally expands. In particular, the anti-fracture layer 270 may offset stress applied to a region of the third ceramic layer 220 corresponding to the edge of the heat dissipation member 230, which may cause enhancement in the durability of the light emitting device package 200.

FIGS. 5A to 5D are views illustrating embodiments of arrangement of the light emitting devices and the sidewall of the cavity sidewall.

Figure 5:
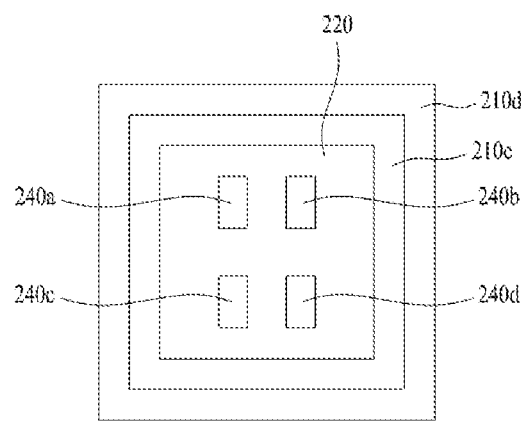
FIGS. 5A to 5D are views illustrating embodiments of arrangement of light emitting devices and a cavity sidewall.
Figure 5:
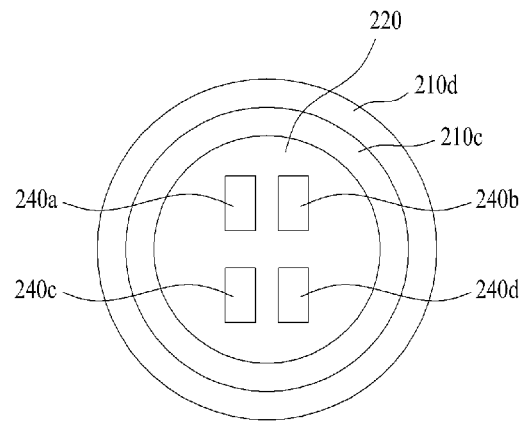
Figure 5:
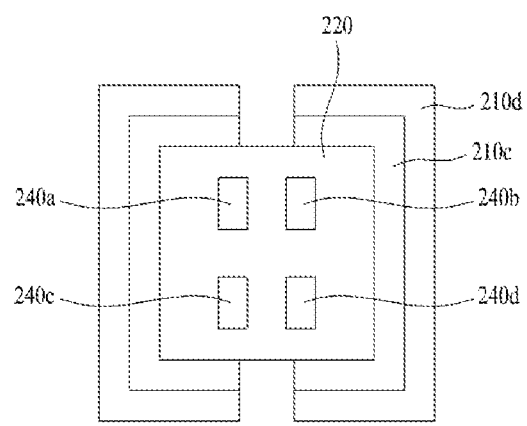
Figure 5:
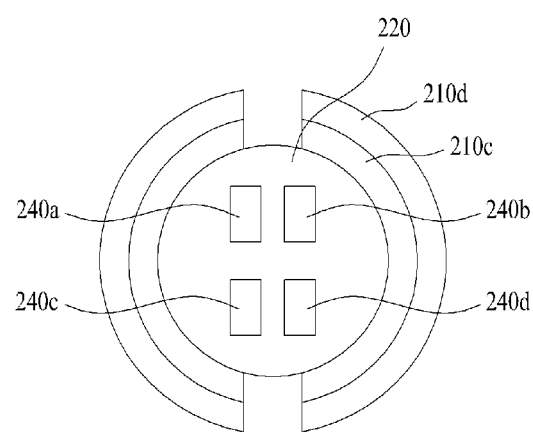

In the embodiment exemplarily shown in FIG. 5A, four light emitting devices 240a to 240d are arranged on the bottom surface of the cavity, i.e. on the third ceramic layer 220, and two first ceramic layers 210c and 210d constitute a rectangular sidewall of the cavity.

In the embodiment exemplarily shown in FIG. 5B, four light emitting devices 240a to 240d are arranged on the bottom surface of the cavity, i.e. on the second ceramic layer 220, and two first ceramic layers 210c and 210d constitute a circular sidewall of the cavity.

The embodiment exemplarily shown in FIG. 5C is similar to the embodiment of FIG. 5A, but a pair of open regions is formed in two facing sides of the two first ceramic layers 210c and 210d constituting the sidewall of the cavity.

The embodiment exemplarily shown in FIG. 5D is similar to the embodiment of FIG. 5B, but a pair of open regions is formed in facing regions of the two first ceramic layers 210c and 210d constituting the sidewall of the cavity.

According to an embodiment, a plurality of light emitting device packages may define an array on a circuit board, and optical members, such as a light guide panel, a prism sheet, and a diffusion sheet, may be arranged on an optical path of the light emitting device packages. The light emitting device packages, the circuit board, and the optical members may function as a light unit. According to another embodiment, a display apparatus, an indicator, or a lighting system including semiconductor devices or light emitting device packages of the above-described embodiments may be realized. For example, a lighting system may include a lamp or a street light. Hereinafter, a backlight unit, a sterilization apparatus, and a lighting apparatus having the above-described light emitting device packages will be described.

Figure 6:
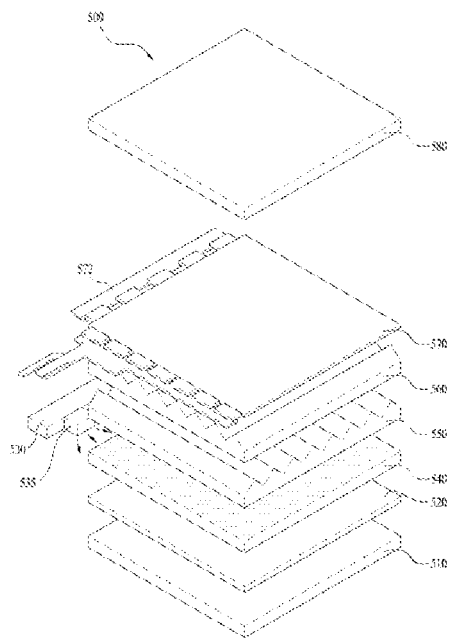
FIG. 6 is a view illustrating an embodiment of an image display apparatus having light emitting device packages.

FIG. 6 is a view illustrating an embodiment of an image display apparatus having light emitting device packages.

As exemplarily shown, the image display apparatus 500 according to the present embodiment includes a light source module, a reflector 520 on a bottom cover 510, a light guide panel 540 placed in front of the reflector 520 to guide light emitted from the light source module in a forward direction of the image display apparatus 500, first and second prism sheets 550 and 560 placed in front of the light guide panel 540, a panel 570 placed in front of the second prism sheet 560, and a color filter 580 placed in front of the panel 570.

The light source module includes a light emitting device package 535 on a circuit board 530. Here, the circuit board 530 may be a Printed Circuit Board (PCB), and the light emitting device package 535 may be as described above with reference to FIG. 2, and in particular may emit visible light. The bottom cover 510 may be configured to receive internal constituent elements of the image display apparatus 500. The reflector 520 may be prepared as a separate component as illustrated in the drawing, or may be a high reflectivity material coated on a rear surface of the light guide panel 540 or a front surface of the bottom cover 510.

The reflector 520 may be formed of an ultrathin material that forms an ultrathin layer and has high reflectivity. For example, the reflector 520 may be formed of polyethylene terephtalate (PET).

The light guide panel 540 serves to scatter light emitted from a light emitting device package module to allow light to be evenly distributed throughout the entire screen of the image display apparatus. Accordingly, the light guide panel 540 may be formed of a material having good refractivity and transmittance. For example, the light guide panel 540 may be formed of polymethylmethacrylate (PMMA), polycarbonate (PC), or polyethylene (PE). If the light guide panel 540 is omitted, an air guide type image display apparatus may be realized.

The first prism sheet 550 may be formed on a surface of a support film using a polymer material having light transmittance and elasticity. The polymer material may contain a prism layer in which a plurality of solid patterns is iteratively formed. Here, the plurality of patterns, as illustrated, may include iterative striped ridges and valleys.

In the second prism sheet 560, the direction of ridges and valleys on a surface of a support film may be perpendicular to the direction of ridges and valleys on the surface of the support film in the first prism sheet 550. This serves to evenly distribute light directed from the light source module and the reflector throughout the panel 570.

In the present embodiment, the first prism sheet 550 and the second prism sheet 560 serve as optical sheets. The optical sheets may have another combination, for example, a micro-lens array, a combination of a diffusion sheet and a micro-lens array, or a combination of a single prism sheet and a micro-lens array.

The panel 570 may be a liquid crystal display panel. Instead of the liquid crystal display panel 570, other kinds of display apparatuses that require a light source may be provided.

The panel 570 is constructed in such a way that liquid crystals are interposed between both glass bodies and polarizers are disposed respectively on the glass bodies to realize light polarization. Here, the liquid crystals have intermediate characteristics between liquid and solid. The liquid crystals, which are organic molecules having fluidity similar to liquid, have a regular molecular arrangement. Thus, the liquid crystals serve to display an image as the molecular arrangement thereof varies by an external electric field.

The liquid crystal display panel used in the display apparatus is of an active matrix type and utilizes a transistor as a switch to adjust a voltage applied to each pixel.

The color filter 580 is provided on a front surface of the panel 570 and serves to selectively transmit light having passed through the panel 570 through Red, Green and Blue pixels, enabling display of an image.

The light emitting device packages arranged at the image display apparatus according to the present embodiment may achieve durability enhancement owing to the third ceramic layer and the anti-fracture layer.

Figure 7:
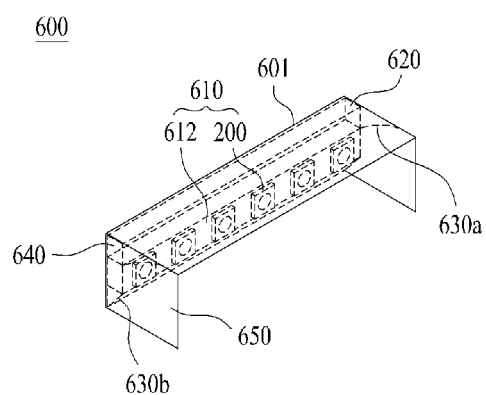
FIG. 7 is a view illustrating an embodiment of a sterilization apparatus having light emitting device packages.

FIG. 7 is a view illustrating an embodiment of a sterilization apparatus having light emitting device packages.

Referring to FIG. 7, the sterilization apparatus 600 may include a light emitting module 610 mounted on a surface of a housing 601, diffusive reflectors 630*a* and 630*b* to implement diffuse reflection of deep-ultraviolet light, and a power supply unit 620 to supply electricity to the light emitting module 610. The light source module 610 may emit near-ultraviolet or deep-ultraviolet light.

First, the housing 601 has a compact rectangular configuration in which the light emitting module 610, the diffusive reflectors 630*a* and 630*b*, and the power supply unit 620 are integrated in the housing 601. The housing 601 may have a shape and constituent material efficient to outwardly radiate heat generated in the sterilization apparatus 600. For example, the housing 601 may be formed of any one material of Al, Cu and alloys thereof. Accordingly, the housing 601 may exhibit enhanced heat transfer efficiency with outside air, thus achieving radiation enhancement.

Alternatively, the housing 601 may have a special external surface shape. For example, an external surface of the housing 601 may have a corrugated shape, a mesh shape, or unspecified convexo-concave shape. This external surface shape may achieve greater heat transfer efficiency between the housing 601 and the outside air, resulting in radiation enhancement.

Attachment plates 650 may be provided respectively at both ends of the housing 601. The attachment plates 650, as exemplarily illustrated, serve as brackets used to secure the housing 601 to equipment. The attachment plates 650 may protrude from both ends of the housing 601 in a given direction. Here, the given direction may be an inward direction of the housing 601 in which deep-ultraviolet emission and diffuse reflection occur.

Accordingly, the attachment plates 650 provided at both ends of the housing 601 provide a securing region with respect to the equipment, thereby allowing the housing 601 to be more effectively secured.

The attachment plates 650 may be secured by any one method selected from among screwing, riveting, adhesive bonding, and separable coupling. These various fastening methods are clearly understood by those skilled in the art and thus a detailed description thereof will be omitted herein.

The light emitting module 610 is mounted on the surface of the above-described housing 601. The light emitting module 610 serves to emit deep-ultraviolet light to perform germicidal sterilization of air. To this end, the light emitting module 610 includes a board 612, and a plurality of light emitting device packages 200 mounted on the board 612. Here, the light emitting device packages 200 are as described above and may exhibit enhanced durability owing to the third ceramic layer and the anti-fracture layer.

The board 612 may be aligned in a single line on an inner surface of the housing 601, and may be a PCB including a circuit pattern (not shown). In addition to a general PCB, the board 612 may include a Metal Core PCB (MCPCB), a flexible PCB, or the like, but the disclosure is not limited thereto.

Next, the diffusive reflectors 630*a* and 630*b* may be plate-shaped reflection members to forcibly implement diffuse reflection of deep-ultraviolet light emitted from the above-described light emitting module 610. The diffusive reflectors 630*a* and 630*b* may have various front plane shapes and arrangements. The diffusive reflectors 630*a* and 630*b* may be designed to have slightly different planar structures (e.g., radii of curvature), thereby emitting diffusively reflected deep-ultraviolet light beams to overlap areas, thus causing increased emission intensity or expansion in the width of an emission region.

The power supply unit 620 serves to supply electricity to the above-described light emitting module 610 upon receiving power. The power supply unit 620 may be located within the aforementioned housing 601. As exemplarily illustrated, the power supply unit 620 may be located closer to an inner wall in a gap between the diffusive reflectors 630*a* and 630*b* and the light emitting module 610. To introduce power from an external source to the power supply unit 620, a power connector 640 for electrical interconnection may be additionally provided.

The power connector 640 may have a planar shape, but may take the form of a socket or cable slot to be electrically connected to a power cable (not shown) of the external power source. The power cable may have a flexible extension configuration to achieve easy connection with the external source.

Figure 8:
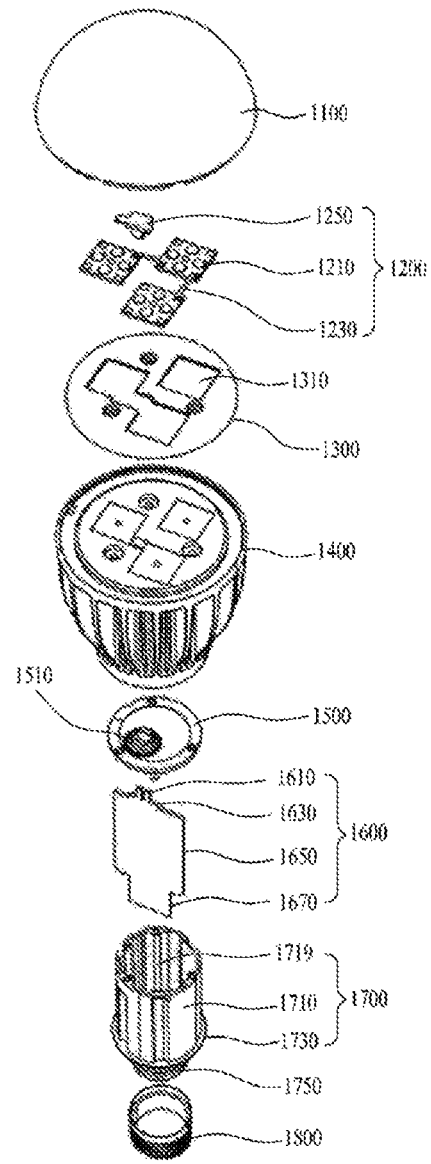
FIG. 8 is a view illustrating an embodiment of a lighting apparatus having light emitting device packages.

FIG. 8 illustrates an embodiment of a lighting apparatus having light emitting device packages.

The lighting apparatus according to the present embodiment may include a cover 1100, a light source module 1200, a heat dissipation member 1400, a power supply unit 1600, an inner case 1700, and a socket 1800. In addition, the lighting apparatus according to the present embodiment may include a member 1300 and/or a holder 1500. The light source module 1200 may emit visible light and include light emitting device packages according to the above-described embodiments. As described above, each light emitting device package may exhibit durability enhancement owing to the third ceramic layer and the anti-fracture layer.

The cover 1100 may take the form of an empty bulb or semi-sphere having a partial open region. The cover 1100 may be optically coupled to the light source module 1200. For example, the cover 1100 may act to diffuse, scatter, or excite light emitted from the light source module 1200. The cover 1100 may be one kind of optical member. The cover 1100 may be coupled to the heat dissipation member 1400. The cover 1100 may have a coupling portion to be coupled to the heat dissipation member 1400.

An inner surface of the cover 1100 may be coated with milky paint. The milky paint may contain a diffuser to diffuse light. The surface roughness of the inner surface of the cover 1100 may be greater than the surface roughness of an outer surface of the cover 1100. This serves to ensure sufficient scattering and diffusion of light from the light source module 1200 and consequently outward emission of the light.

The cover 1100 may be formed of glass, plastics, polypropylene (PP), polyethylene (PE), polycarbonate (PC), or the like. Here, polycarbonate has excellent light-resistance, heat-resistance and strength. The cover 1100 may be transparent to allow the light source module 1200 to be visible from the outside, or may be opaque. The cover 1100 may be formed by blow molding.

The light source module 1200 may be arranged on a surface of the heat dissipation member 1400. Thus, heat of the light source module 1200 is transferred to the heat dissipation member 1400. The light source module 1200 may include light emitting device packages 1210, connection plates 1230, and a connector 1250.

A fluorescent substance may be placed at a surface of the above-described cover 1100, or may be placed in the light emitting device package 1210. Assuming that the fluorescent substance is placed in the light emitting device package 1210, for example, red, green, and blue fluorescent substances may be placed on separate light emitting devices, or a mixture of red, green, and blue fluorescent substances may be placed on the respective light emitting devices. The member 1300 may be placed on an upper surface of the heat dissipation member 1400, and may include guide recesses 1310 into which the plurality of light emitting device packages 1210 and the connector 1250 are inserted. The guide recesses 1310 correspond to substrates of the light emitting device packages 1210 and the connector 1250.

A light reflection material may be coated over a surface of the member 1300. For example, white paint may be coated over the surface of the member 1300. The member 1300 reflects light, reflected from the inner surface of the cover 1100 and returned to the light source module 1200, to the cover 1100. In this way, the lighting apparatus according to the embodiment may achieve enhanced light efficiency.

The member 1300 may be formed of an insulating material, for example. The connection plates 1230 of the light source module 1200 may be formed of an electrically conductive material. Accordingly, electrical connection between the heat dissipation member 1400 and the connection plate 1230 may be accomplished. The member 1300, formed of an insulating material, may prevent electrical short-circuit between the connection plates 1230 and the heat dissipation member 1400. The heat dissipation member 1400 acts to radiate heat upon receiving heat from the light source module 1200 and heat from the power supply unit 1600.

The holder 1500 is configured to block an accommodation recess 1719 of an insulating portion 1710 of the inner case 1700. Accordingly, the power supply unit 1600 accommodated in the insulating portion 1710 of the inner case 1700 is sealed. The holder 1500 has a guide protrusion 1510. The guide protrusion 1510 has a hole through which a protrusion 1610 of the power supply unit 1600 passes.

The power supply unit 1600 processes or converts electric signals received from an external source to thereby transmit the same to the light source module 1200. The power supply unit 1600 is accommodated in the accommodation recess 1719 of the inner case 1700, and is sealed within the inner case 1700 by the holder 1500. The power supply unit 1600 may include the protrusion 1610, a guide portion 1630, a base 1650, and an extension 1679.

The guide portion 1630 is configured to outwardly protrude from one side of the base 1650. The guide portion 1630 may be inserted into the holder 1500. A plurality of elements may be arranged on a surface of the base 1650. The plurality of elements, for example, may include a direct current (DC) converter to convert alternating current (AC) power supplied from an external power source into DC power, a drive chip to control driving of the light source module 1200, and an electrostatic discharge (ESD) protector to protect the light emitting module 1200, but the disclosure is not limited thereto.

The extension 1670 is configured to outwardly protrude from the other side of the base 1650. The extension 1670 is inserted into a connection portion 1750 of the inner case 1700 and is adapted to receive electric signals from an external source. For example, the extension 1670 may have a width equal to or less than a width of the connection portion 1750 of the inner case 1700. One end of each of a "+" electric wire and a "−" electric wire may be electrically connected to the extension 1670, and the other end of each of the "+" electric wire and the "−" electric wire may be electrically connected to the socket 1800.

The inner case 1700 may contain the power supply unit 1600 and a molding part therein. The molding part is formed through hardening of a molding liquid, and serves to allow the power supply unit 1600 to be secured within the inner case 1700.

In the above-described lighting apparatus, UV light emitted from the light emitting devices of the light emitting device packages causes light emission of red, green, and blue wavelengths from fluorescent substances, resulting in emission of white light. In this way, superior color reproduction than light emitting device packages using a blue light emitting device and yellow fluorescent substance may be accomplished.

As is apparent from the above description, light emitting device packages according to the embodiments may be configured in such a manner that a third ceramic layer and a anti-fracture layer may endure stress caused by thermal expansion of a heat dissipation member even if the heat dissipation member thermally expands after implementation of a co-firing process upon fabrication of the package. In particular, the anti-fracture layer may offset stress applied to the third ceramic layer at a region corresponding to an edge of the heat dissipation member, which may enhance seal durability of the light emitting device package.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A light emitting device package comprising:
a package body including ceramic material and a cavity;
a pad disposed at the package;
a light emitting device electrically connected to the pad;
a metal layer inserted into the package body and including a body, an upper surface and a lower surface; and
an electrode disposed at the package body,
wherein the pad vertically overlaps with the metal layer,
wherein the light emitting device emits light in a wavelength range of 190 nm to 290 nm,
wherein the light emitting device has a first conductive type semiconductor layer, a second conductive type semiconductor layer, an active layer including an AlGaN barrier layer disposed between the first conductive type semiconductor layer and the second conductive type semiconductor layer, and a conductive clad layer including AlGaN or InAlGaN disposed on the active layer,
wherein a portion of the package body is disposed between the light emitting device and the metal layer,
wherein at least one width of the upper surface and the lower surface of the metal layer is wider than a width of the body of the metal layer, and
wherein the upper surface of the metal layer has a first part and the first part is provided outwardly from a side surface of the body of the metal layer, the lower surface of the metal layer has a second part and the second part is provided outwardly from the side surface of the body of the metal layer, and a width of the first part and a width of the second part are different.

2. The light emitting device package according to claim 1, wherein the cavity has a first side surface and a second side surface, and a width between the first side surface and the second side surface of the cavity is narrower than a maximum width of the metal layer.

3. The light emitting device package according to claim 1, wherein the cavity includes a first cavity and a second cavity, the pad is disposed on a bottom surface of the first activity, the light emmitting device is disposed on the second cavity, the first cavity has a step portion, and the scond cavity is provided at the bottom surface of the first cavity.

4. The light emitting device package according to claim 1, wherein the width of the upper surface of the metal layer is narrower than the width of the lower surface of the metal layer.

5. The light emitting device package according to claim 1, wherein the width of the upper surface of the metal layer is wider than the width of the lower surface of the metal layer.

6. The light emitting device package according to claim 1, wherein the width of the upper surface of the metal layer is different from the width of the lower surface of the metal layer.

7. The light emitting device packaged according to claim 1, wherein a width of a top open region of the cavity is wider than a width of a bottom surface of the cavity.

8. The light emitting device package according to claim 1, wherein the electrode has a first portion and a second portion vertically overlaps with the first portion, and the first portion is disposed in the package body and the second portion is disposed under a bottom surface of the package body.

9. The light emitting device package according to claim 1, further comprising an adhesive layer disposed between the light emitting device and the package body.

10. The light emitting device package according to claim 3, wherein a top surface of the light emitting device is disposed above the second cavity.

11. The light emitting device package according to claim 10, wherein the bottom surface of the electrode is disposed under the bottom surface of the package body.

12. The light emitting device package according to claim 3, wherein the pad is spaced apart from an edge of the second cavity.

13. A light emitting device package comprising:
a package body including ceramic material and a cavity;
a pad disposed at the cavity;
a light emitting device disposed on the cavity and electrically connected to the pad;
an adhesive layer disposed between the light emitting device and a bottom surface of the cavity:
a metal layer inserted into the package body and including a center portion, a first expanded portion and a second expanded portion, wherein the center portion has a region disposed under the light emitting device; and
an electrode disposed at the package body,
wherein the metal layer is disposed under the cavity,
wherein the light emitting device emits light in a wavelength range of 190 nm to 397 nm,
wherein the first expanded portion is disposed at an upper edge of the center portion,
wherein the second expanded portion disposed at a lower edge of the center portion,
wherein the first expanded portion and the second expanded portion are provided at a same side surface from the center portion,
wherein a width of the first expanded portion and a width of the second expanded portion are different,
wherein a width of the center portion is wider than a width of the first expanded portion or the second expanded portion,
wherein the cavity has a first side surface and a second side surface, and
wherein at least one of a width between the first side surface of the cavity or a width of the second side surface of the cavity is narrower than a width of the metal layer.

14. The light emitting device package according to claim 13, wherein a portion of the package body is disposed between the adhesive layer and the metal layer, and wherein the portion of the package body is composed of same material as the other portion of the package body.

15. The light emitting device package according to claim 13, wherein the cavity has a step portion, and wherein the step portion has a flat bottom surface.

16. The light emitting device package according to claim 13, wherein the electrode has a first portion and a second portion, the first portion is disposed in the package body and the second portion disposed under a bottom surface of the package body, and the first portion of electrode vertically overlaps with the second portion of the electrode.

17. The light emitting device package according to claim 13, wherein the pad vertically overlaps with the metal layer and is spaced apart from an edge of the second cavity.

18. The light emitting device package according to claim 13, wherein a top surface of the light emitting device is disposed above a top surface of the second cavity, and the bottom surface of the elctrode is disposed under the bottom surface of the package body.

19. The light emitting device package according to claim 13, wherein a top surface of the pad is disposed above a top surface of the adhesive layer, and a top surface of the light emitting device is disposed above the top surface of the pad.

20. The light emitting device package according to claim 13, wherein the light emitting device has a conductive layer and a light emitting structure, the light emitting structure having an active layer, wherein the conductive layer is disposed on the active layer, and wherein the conductive layer includes AlGaN or InAlGaN.

21. A light emitting device package comprising:
a package body including an accommodation space and the accommodation space having a first bottom surface, a second bottom surface, a first side surface and a second side surface;
a pad disposed on the first bottom surface;
a light emitting device disposed on the second bottom surface and electrically connected to the pad;
an adhesive layer disposed between the light emitting device and the second bottom surface;
a metal layer inserted into package body and the metal layer including a body, a upper surface and a lower surface; and
an electrode disposed at the package body;
wherein the first bottom surface is disposed above the second bottom surface,
wherein the first side surface is disposed above the second side surface,
wherein a width of the first bottom surface is wider than a width of the second bottom surface, wherein a portion of the package body is disposed between the adhesive layer and the metal layer:

wherein at least one width of the upper surface and the lower surface of the metal layer is wider than a width of the body of the metal layer, wherein the width of the second bottom surface is narrower than a width of the metal layer, and wherein the package body has a layer, a side surface of the layer is the second side surface of the accommodation space, and the layer vertically overlaps with the metal layer.

* * * * *